US012617753B2

(12) United States Patent
Mason

(10) Patent No.: US 12,617,753 B2
(45) Date of Patent: May 5, 2026

(54) UREA DERIVATIVES AND THEIR USE AS CURATIVES AND CURATIVE ACCELERATORS FOR RESIN SYSTEMS

(71) Applicant: HEXCEL COMPOSITES LIMITED, Duxford (GB)

(72) Inventor: Christopher Mason, Cambridgeshire (GB)

(73) Assignee: HEXCEL COMPOSITES LIMITED, Duxford (GB)

( * ) Notice: Subject to any disclaimer, the term of this patent is extended or adjusted under 35 U.S.C. 154(b) by 468 days.

(21) Appl. No.: 18/041,065

(22) PCT Filed: Aug. 12, 2021

(86) PCT No.: PCT/EP2021/072561

§ 371 (c)(1),
(2) Date: Feb. 8, 2023

(87) PCT Pub. No.: WO2022/034201

PCT Pub. Date: Feb. 17, 2022

(65) Prior Publication Data

US 2024/0262790 A1 Aug. 8, 2024

(30) Foreign Application Priority Data

Aug. 13, 2020 (GB) ...................................... 2012669

(51) Int. Cl.

*C07C 275/40* (2006.01)
*C08G 59/40* (2006.01)
*C08J 5/24* (2006.01)

(52) U.S. Cl.

CPC ........ *C07C 275/40* (2013.01); *C08G 59/4021* (2013.01); *C08J 5/24* (2013.01); *C08J 2363/00* (2013.01)

(58) Field of Classification Search

None
See application file for complete search history.

(56) References Cited

U.S. PATENT DOCUMENTS

| | | | |
|---|---|---|---|
| 4,404,356 | A | 9/1983 | Andrews |
| 4,507,445 | A | 3/1985 | Andrews |
| 5,294,530 | A | 3/1994 | Seto et al. |
| 9,663,609 | B2 | 5/2017 | Eichhorn et al. |

FOREIGN PATENT DOCUMENTS

| | | | |
|---|---|---|---|
| EP | 0985692 | B1 | 1/2005 |
| JP | 2005084469 | A | 3/2005 |
| JP | 2005241691 | A | 9/2005 |
| WO | 2014062531 | A2 | 4/2014 |

OTHER PUBLICATIONS

Dominguez et al. (European Polymer Journal, 2010, vol. 46, Issue 1, p. 50-57) (Year: 2010).*

Machine English translation of Goto et al. (JP 2005084469, pub date Mar. 31, 2005) (Year: 2005).*

International Search Report (ISR), issued in the parent Patent Cooperation Treaty (PCT), Application No. PCT/EP2021/072561, mailed on Nov. 26, 2021.

Search Report, issued in the priority GB Application No. GB2012669.4, mailed on Jan. 27, 2021.

Database Registry (online), Chemical Abstracts Service, Columbus, Ohio, US; Jan. 16, 2002; "N,N"-[sulfonylbis(6- hydroxy-3, 1-phenylene)]bis[N'-(2-chlorophenyl)-urea", RegistryJan. 16, 2002 (Jan. 16, 2002), Database Accession No. 383390-39-4.

* cited by examiner

*Primary Examiner* — Renee Claytor
*Assistant Examiner* — Jennifer C Sawyer
(74) *Attorney, Agent, or Firm* — W. Mark Bielawski

(57) ABSTRACT

Bisorthohydroxy aromatic urones and their use as curatives and cure accelerators in resin systems particularly epoxy resin systems provide formulations with good outlife, low curing temperatures and desirable glass transition temperatures after curing, they are particularly useful in prepregs used in the production of components for the aerospace and wind turbine industries.

2 Claims, 2 Drawing Sheets

UREA DERIVATIVES AND THEIR USE AS CURATIVES AND CURATIVE ACCELERATORS FOR RESIN SYSTEMS

The present invention relates to novel derivatives of urea, their use as curatives or curative accelerators for resin systems particularly epoxy resins, epoxy resin formulations containing the derivatives of urea and prepregs and moulded articles employing such epoxy resin formulations. Accordingly the invention provides novel urea based compounds, a curative system, a resin formulation, a cured resin, a use, a composite and a moulding material.

Adipic acid dihydrazide and isophthalic acid dihydrazide are known as curatives for epoxy resin formulations. It has been suggested that they may be used together with accelerators such as urea based materials as is disclosed in U.S. Pat. Nos. 4,404,356 and 4,507,445. However there remains a need for curatives, which enable the combination of storage stability of the resin formulation prior to cure, low temperature cure, fast cure to produce a cured resin having a high glass transition temperature (Tg) and which also retains the Tg over a period of time particularly when subjected to moisture particularly at elevated temperatures. One object of the present invention is therefore to provide a curable epoxy resin composition having excellent storage stability, enhanced curing characteristics including low temperature and faster cure and which provides a cured product having excellent mechanical properties.

A curative is a compound which is adapted to initiate or advance a polymerisation reaction of a polymerisable resin. An accelerator is a compound which enhances the polymerisation reaction (or "curing") caused by a curative.

The curing of epoxy resins is usually an exothermic reaction and it is important that the reaction is controlled to avoid excess temperatures that can degrade the epoxy material and can cause stress and deformation such as cracking in articles and components created from the epoxy containing formulation. There is however an ongoing need to increase the Tg of cured epoxy resins particularly to provide sufficient strength to the articles and components particularly when the resins are being used in resin impregnated fibre reinforcements sometimes known as prepregs that are used to produce larger and larger articles and particularly thicker articles made from stacks of prepregs such as stacks of more than 40, sometimes more than 60 up to 80 prepregs especially in the production of components for the aerospace and wind turbine industries. A prepreg comprises a fibrous reinforcement impregnated with a curable resin ready for curing within a mould or vacuum bag. To date a higher Tg has been obtained using higher curing temperatures and/or longer curing cycles and employing hardeners such as dicyandiamide which require higher curing temperatures; however, this increases the risk of high temperature degradation of the resin.

It has been proposed that the use of urones as curatives can enable higher Tgs to be obtained using lower cure temperatures and shorter cure cycles.

Derivatives of urea are known as is their use as curatives for epoxy resins and such derivatives are sometimes known as urones. U.S. Pat. No. 4,404,356 relates to hydroxy phenyl ureas of formula

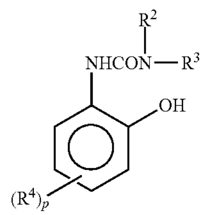

and to their use as accelerators for heat curing of epoxy resins and also to their use as primary curing agents for epoxy resins.

U.S. Pat. No. 9,663,609 relates to the use of bis or multifunctional N,N'-(Dimethyl) urones and a method for curing epoxy resin compositions using such urones. The use of these materials is said to provide a method for the controlled curing of epoxy resins particularly for solid components having large layer thickness of epoxy resins to avoid internal stresses or other thermal damage in mouldings or components that are produced therefrom. The bis- or multi-functional N,N'-(dimethyl) urones are of the general formula $$R—(NH—CO—N(CH3)2)n$$

where R is a linear or branched aliphatic radical or an unsubstituted, halo substituted and/or alkyl substituted aromatic radical and n is a number from 2 to 20.

However, U.S. Pat. No. 9,663,609 does not envisage that when R is an aromatic radical it can be hydroxy substituted. The use of the bis- or multifunctional orthohydroxy aromatic urones according to this invention as curatives or curative accelerators provides a further improvement in the control of the curing of epoxy resins particularly in prepregs.

We have now produced bisfunctional orthohydroxy aromatic urones and we have found that when used as curatives for epoxy resins, the resin can be cured at lower temperatures, such as an externally applied temperature from 80° C. to 150° C. to produce a cured epoxy resin having a higher Tg at complete cure than is produced from the non-hydroxy substituted aromatic bisfunctional urones such as those described in U.S. Pat. No. 9,663,609 and the hydroxyl phenyl ureas of U.S. Pat. No. 4,404,356. The urones of this invention may also be used as accelerators for other epoxy curatives when the curing temperature may be higher for example up to 180 C.

In one embodiment the invention therefore provides bisfunctional and multifunctional orthohydroxy aromatic urones, their use as a curative for epoxy resins, their use as accelerators for other curatives for epoxy resins, epoxy resin formulations containing the bisfunctional and multifunctional orthohydroxy nurones, the use of such formulations as a resin matrix for reinforcing fibres particularly in prepregs and fibre reinforced materials made therefrom.

The invention therefore provides bis functional and multifunctional orthohydroxy aromatic urones of the formulae selected from (i)

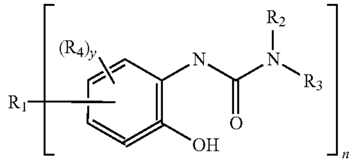

(ii)

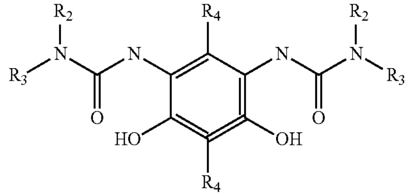

(iii)

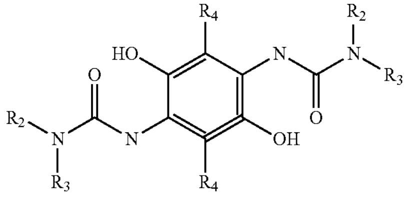

Where $R_1$═S, SO2, SO, P, PX, N, NH, NX, P═O(OX or OH), C═O, a linear or branched aliphatic radical (substituted or unsubstituted), or an unsubstituted, halo substituted and/or alkyl substituted aromatic radical and n is a number from 2 to 20.

Where X=a linear or branched aliphatic radical (substituted or unsubstituted), or an unsubstituted, halo substituted and/or alkyl substituted aromatic radical $R_2$ and $R_3$═ at each occurrence, independently of one another, selected from an alkyl, cycloalkyl, alkenyl, cycloalkenyl, or aralkyl group, which may be substituted by a halogen atom (preferably a chlorine atom) or by a hydroxyl or cyano group, with the proviso that R may alternatively denote a hydrogen atom, or $R_2$ and $R_3$ together with the indicated attached nitrogen atom denote a heterocyclic ring containing 3 to 5 carbon atoms, and optionally one oxygen atom.

$R_4$═ at each occurrence, independently of one or another, is selected from H, $NH_2$, $NO_2$, nitrile, a halogen, linear or branched aliphatic radical, or an unsubstituted, halo substituted and/or alkyl substituted aromatic radical, and Y=1 to 3.

The compounds of this invention may be used as curatives or accelerators for other curatives or they can perform both of these functions particularly with epoxy resins and the invention also provides an epoxy resin formulation containing one or more of the compounds of this invention optionally together with one or more other curatives.

Where the urea derivatives of this invention are used as the primary or sole curative for the resin we prefer to use from 2 to 20 wt % of the urea derivative based on the weight of the resin more preferably 5 to 15 wt %.

The use of the urea derivatives of this invention as primary or sole curatives in thermosetting resin systems has produced a material which can be stored for several weeks without significant cure (known as the outlife of the system) and which produces a cured resin having a desirable Tg for applications such as prepregs used to make components for the aerospace and wind energy industries particularly when the components are thick and made from a stack of several layers of the prepreg. Typically, at least 40 layers and sometimes 60 or more layers.

The use of the curative also allows improved control of the heat generated during the curing reaction to avoid the risk of reaction run away which can cause degradation of the resin and damage to the cured article.

The compounds of this invention may also be used as accelerators for other curatives for epoxy resins. Examples of curatives whose performance can be accelerated by the compounds of this invention are primary or secondary amines. The amines may be aliphatic, cycloaliphatic, aromatic, or aromatic structures having one or more amino moieties.

Exemplary amine curing agents include ethylenediamine, diethylenediamine, diethylenetriamine, triethylenetetramine, propylene diamine, tetraethylenepentamine, hexaethyleneheptamine, hexamethylenediamine, cyanoguanidine, 2-methyl-1,5-pentamethylene-diamine, 4,7,10-trioxatridecan-1,13-diamine, aminoethylpiperazine, and the like. Exemplary curing agents include dicyanopolyamides, most preferably (DICY). 4,4'-diaminodiphenyl sulfone (4,4'-DDS) or 3,3'-diaminodiphenyl sulfone (3,3'-DDS) can also be beneficially employed as a latent amine curing agent, as well as mixtures of DICY and DDS. Dihydrazides such and ADH, IDH and polyamines such as Ancamine 2441 and BF3-MEA complexes such as Anchor 1040 (Air Products) are also suitable as a latent curing agent.

In some embodiments, the amine curing agent is a polyether amine having one or more amine moieties, including those polyether amines that can be derived from polypropylene oxide or polyethylene oxide. Commercially available polyether amines include the polyether polyamines (available under the trade designation "JEFFAMINE" from Huntsman Corporation and 4,7,10-trioaxatridencane-1,13-diamine (TTD) (available from BASF). A preferred latent amine curing agent is Dyhard 100E from AlzChem.

Preferred other curatives are amino sulfones such as 4,4 diaminodiphenyl sulfone (sometimes known as 4,4-DDS) and 3,3 diaminodiphenyl sulfone (sometimes known as 3,3-DDS) which are typically used as curatives in resin formulations used in the production of aerospace components.

When the compounds of this invention are used as accelerators for other curatives a smaller amount based on the weight of epoxy resin may be used than when the compound is the primary or sole curative. For this use we prefer to use from 0.1 to 1.5 wt % more preferably 0.2 to 1 wt % based on the weight of epoxy resin.

In a further embodiment of the invention there is provided a resin formulation comprising the bisorthohydroxy aromatic urone in combination with at least one resin component such as an epoxy, polyisocyante and a phenolic resin particularly an epoxy resin. The resin formulation is preferably in the form of a one-component resin formulation which does not require any further mixing of components before its use.

In a further embodiment there is provided a resin formulation comprising a curable resin such as an epoxy, polyisocyante and a phenolic resin containing a curative other than a bisorthohydroxy aromatic urone of this invention together with a bisorthohydroxy aromatic urone of this invention which acts as an accelerator for the curative.

In a further embodiment the invention provides the use of a resin formulation of this invention as a matrix in fibre reinforced composites which may be a prepreg or may be obtained by resin infusion of dry fibrous material laid up in a mould with the resin formulation. The invention further provides a fibre reinforced composite obtained by the thermal curing of such a resin matrix which can be accomplished in a press or in a vacuum bag.

The cured Tg of a resin is measured in accordance with ASTM D7028 (Glass Transition Temperature (DMA Tg) of Polymer Matrix Composites by Dynamic Mechanical Analysis (DMA))

The heat released during the curing reaction is related to the total heat for fully curing and can be measured using Digital Scanning calorimetry as follows. A reference resin sample is heated from 10° C. to 350° C. at 10° C./min rate to full cure (100%) and the generated heat ΔHi is recorded. The degree of cure of a particular resin sample of the same composition as the reference resin sample can then be measured by curing the sample to the desired temperature and at the desired rate and for the desired time by heating the sample at these conditions and measuring the heat ΔHe generated by this cure reaction. The degree of cure (Cure %) is then defined by:

$$\text{Cure \%} = [(\Delta Hi - \Delta He) / \Delta Hi] \times 100\ [\%]$$

where ΔHi is the heat generated by the uncured resin heated from 10° C. up to fully cured at 350° C. and ΔHe the heat generated by the certain degree cured resin heated up to a desired temperature and rate.

In another embodiment of the invention there is provided a moulding material comprising the thermosetting resin formulation of this invention in combination with a fibrous reinforcement material. The fibrous reinforcement material may be provided: as a woven fabric or a multi-axial fabric to form a prepreg, as individual fibre tows for impregnation with the resin composition to form towpregs, or as chopped fibres, short fibres or filaments to form a moulding compound. The preferred fibrous material is selected from carbon fibre, glass fibre, aramid and mixtures thereof. The moulding material may be constructed from a cast resin film which contains the resin formulation and which is combined with a fibrous reinforcement layer. Preferably the resin film impregnates the fibrous reinforcement which may be accomplished by pressing a layer of resin onto the fibrous material or by infusion of the resin into fibrous material within a mould.

In a further embodiment of the invention there is provided an adhesive comprising a resin formulation of this invention in combination with at least one filler.

The compositions of this invention are storage stable at ambient temperature prior to curing and are capable of fast curing at relatively low temperatures, such as 80° C. to 150° C. whilst the Tg, the retained Tg and the mechanical properties of the cured resin enable use of the cured resin formulation in industrial structural applications particularly as fibre reinforced materials which are useful as automotive and aerospace structural components as well as sporting goods and wind turbine components.

Where the resin is an epoxy resin it may be monofunctional or multifunctional, preferably at least difunctional. In an embodiment, the epoxy resin component (A) may be selected from various conventionally-known polyepoxy compounds. Examples thereof include: aromatic glycidyl ether compounds such as bis(4-hydroxyphenyl)propane diglycidyl ether, bis(4-hydroxy-3,5-dibromophenyl) propane diglycidyl ether, bis(4-hydroxyphenyl)ethane diglycidyl ether, bis(4-hydroxyphenyl)methane diglycidyl ether, resorcinol diglycidyl ether, phloroglucinol triglycidyl ether, trihydroxy biphenyl triglycidyl ether, tetraglycidyl benzophenone, bisresorcinol tetraglycidyl ether, tetramethyl bisphenol A diglycidyl ether, bisphenol C diglycidyl ether, bisphenol hexafluoropropane diglycidyl ether, 1,3-bis[1-(2,3-epoxypropoxy)-1-trifluoromethyl-2,2,2-trifluoroethyl] benzene, 1,4-bis[1-(2,3-epoxypropoxy)-1-trifluoromethyl-2,2,2-trifluoromethyl]benzene, 4,4'-bis(2,3-epoxypropoxy) octafluorobiphenyl, and phenolic novolac type bisepoxy compounds; alicyclic polyepoxy compounds such as alicyclic diepoxy acetal, alicyclic diepoxy adipate, alicyclic diepoxy carboxylate, and vinylcyclohexene dioxide; glycidyl ester compounds such as diglycidyl phthalate, diglycidyl tetrahydrophthalate, diglycidyl hexahydrophthalate, dimethylglycidyl phthalate, dimethylglycidyl hexahydrophthalate, diglycidyl-p-oxybenzoate, diglycidylcyclopentane-1,3-dicarboxylate, and dimer acid glycidyl ester; glycidyl amine compounds such as diglycidyl aniline, diglycidyl toluidine, triglycidyl aminophenol, tetraglycidyl diaminodiphenyl methane, and diglycidyl tribromoaniline; and heterocyclic epoxy compounds such as diglycidylhydantoin, glycidyl glycidoxyalkylhydantoin, and triglycidyl isocyanurate; and oligomer compounds thereof.

Examples of the liquid epoxy resin include polyalkylene ether type epoxy compounds such as (poly)ethylene glycol diglycidyl ether, (poly)propylene glycol diglycidyl ether, and trimethylolpropane triglycidyl ether; glycidyl ester type epoxy compounds such as dimer acid diglycidyl ester, phthalic acid diglycidyl ester, and tetrahydrophtalic acid diglycidyl ester; and homopolymers of glycidyl (meth) acrylate, allyl glycidyl ether and the like or copolymers of these monomers with other soft unsaturated monomers. In this context, soft unsaturated monomer refers to a monomer which contains a homopolymer which has a glass transition temperature of less than 60° C. Examples of soft unsaturated monomers include methyl acrylate, ethyl acrylate, butyl (meth)acrylate, isobutyl(meth)acrylate, 2-ethylhexyl(meth) acrylate, and lauryl methacrylate.

A liquid curable epoxy resin composition of the present invention is particularly useful as a one-component liquid epoxy resin prepreg matrix resin formulation which is excellent in both storage stability and curing characteristics and provides a cured product having excellent characteristics, particularly organic solvent resistance.

When the epoxy resin composition of the present invention is used as a prepreg resin formulation, known additives such as fillers, viscosity modifiers, tougheners, pigments, thixotropic agents, and fire retardants, or the like can be optionally mixed into the formulation to enhance its mechanical performance and flow behaviour during cure.

The compositions of this invention may include other typical additives used in thermosetting resin formulations such as impact modifiers, fillers, antioxidants and the like.

The preferred urone of this invention is N,N'-[propylene (4-hydroxy-3,1-phenylene)]bis(N,N-dimethyl)urea. When used as the primary or sole curative for the resins the urones of this invention are preferably present in the epoxy resin composition of the invention in an amount relative to the total weight to 2 to 20 wt % and more preferably 3 to 12 weight %, most preferably in an amount of the total weight of the composition with respect to 4 to 8 wt %.

The bisfunctional orthohydroxy aromatic urones of this invention may be prepared from a precursor obtained by the reaction of 2,2-bis(3-amino-4-hydroxyphenyl)propane and 1,1'-carbonyldiimidazole to produce the bisbenxozolinone precursor of formula

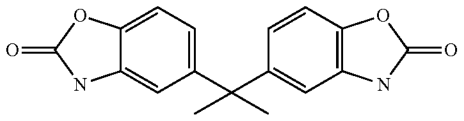 [SMILES: CC(C)(c1ccc2oc(=O)[nH]c2c1)c1ccc2oc(=O)[nH]c2c1]

This precursor may be reacted with dimethylamine to produce N,N'-[propylene(4-hydroxy-3,1-phenylene)]bis(N,N-dimethyl)urea of formula

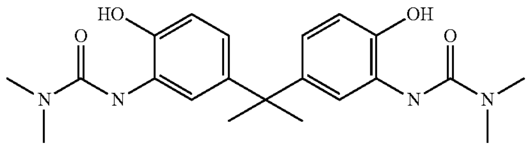

Hereinafter known as PBOHFU.

A bis- or multi-functional orthohydroxy aromatic urone of this invention has the structure represented by formulae (i)

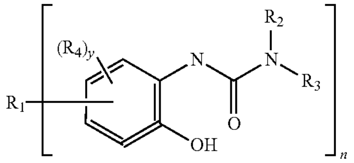

(ii)

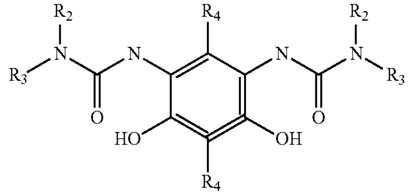

(iii)

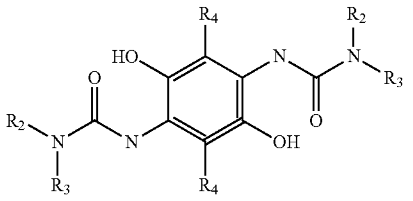

Where $R_1$=S, SO2, SO, P, PX, N, NH, NX, P=O(OX or OH), C=O, a linear or branched aliphatic radical (substituted or unsubstituted), or an unsubstituted, halo substituted and/or alkyl substituted aromatic radical and n is a number from 2 to 20.

Where X=a linear or branched aliphatic radical (substituted or unsubstituted), or an unsubstituted, halo substituted and/or alkyl substituted aromatic radical $R_2$ and $R_3$= at each occurrence, independently of one another, selected from an alkyl, cycloalkyl, alkenyl, cycloalkenyl, or aralkyl group, which may be substituted by a halogen atom (preferably a chlorine atom) or by a hydroxyl or cyano group, with the proviso that $R_2$ may alternatively denote a hydrogen atom, or $R_2$ and $R_3$ together with the indicated attached nitrogen atom denote a heterocyclic ring containing 3 to 5 carbon atoms, and optionally one oxygen atom, in the ring.

$R_4$= at each occurrence, independently of one or another, selected from H, $NH_2$, $NO_2$, nitrile, a halogen, linear or branched aliphatic radical, or an unsubstituted, halo substituted and/or alkyl substituted aromatic radical, and Y=1 to 3.

The functionality is determined solely by the number of urea substituents or radicals. Furthermore, a urea substituent or radical is a radical or substituent according to formula- $$(NH—CO—N(R)_2)$$

The radical $R_1$ in compounds of formula (i) is a bridging unit selected from S, SO2, SO, P, PX, N, NH, NX, P=O(OX or OH), C=O, a linear or branched aliphatic radical (substituted or unsubstituted), or an unsubstituted, halo substituted and/or alkyl substituted aromatic radical. Where X=a linear or branched aliphatic radical (substituted or unsubstituted), or an unsubstituted, halo substituted and/or alkyl substituted aromatic radical.

According to the present invention, n in formula (i) can denote a number from 2 to 20, that is to say compounds having from 2 to 20 urea radicals can be used according to the invention. Preferably n is an integer from 2 to 10 and more preferably n is an integer from 2 to 8, and yet more preferably n is 2 or 3. Accordingly, there can be used according to the present invention in particular diurones, triurones or oligourones of the general formula (i), or mixtures thereof, having two, three or up to 20 dimethylurea radicals. Particular preference is given to diurones where n=2 and triurones where n=3. Moreover, preference is also given to oligourones where n=from 4 to 20, wherein n can be a number from 4 to 20. It is to be emphasised that the choice of the basic structure is of lesser importance.

In another embodiment of the invention as shown by the compounds of formulae (ii) and (iii) the bisfunctional orthohydroxy aromatic urone may comprise a single aromatic moiety to which are attached two urea substitutes having hydroxyl groups in the ortho position to the urea substituents.

It has been found according to the invention in particular that urones of the general formula can be used as the sole curing agents in epoxy resin compositions. Accordingly, in this embodiment these epoxy resin compositions can be free of further curing agents, co-curing agents, curing accelerators and/or catalysts for the curing of epoxy resins.

The amount of the compounds of this invention that is used in the resin formulation depends upon the required function of the compound and depending upon whether it is used as the primary or sole curative or as an accelerator for another curative. The amount can range from 0.01 to 20 parts of the urone of this invention or mixtures thereof per 100 parts of resin, preferably from 0.1 to 15 parts, preferably from 1 to 15 parts and most particularly preferably from 2 to 15 parts per 100 parts of resin. Also preferred are amounts in which there are used, per 100 parts of resin, from 1 to 12 parts, in particular from 2 to 12 parts, more preferably from 3 to 12 parts, particularly preferably from 4 to 12 parts and most particularly preferably from 5 to 12 parts of the urone of the invention.

With these amounts it is possible according to the invention to generate, at a temperature of from 60 to 180° C., a maximum heat flow in the epoxy resin composition of from 0.05 to 0.99 W/g (based on the mass of epoxy resin), so that the epoxy resin composition cures fully.

We have found that the use of the compounds of this invention as primary curatives for epoxy resin compositions enables curing at a temperature of from 60 to 190° C. in particular 60° C. to 180° C., in particular from 60 to 160° C.

and most particularly preferably from 60 to 150° C., and that the curing reaction is controlled so that the epoxy resin composition cures fully without the generation of excess heat that can damage the resin and articles made therefrom. Where the compounds are used as accelerators for other curatives the curing temperature may be at the higher end of the range such as from 150 to 190° C. particularly 60° C. to 180° C.

An epoxy resin composition is considered to be fully cured if the epoxy resin composition cures to the extent of ≥80%, preferably ≥90%, more preferably ≥95%, yet more preferably ≥98%, in particular ≥99% and most preferably 100%. Accordingly, the epoxy groups in the cured epoxy resin composition have reacted to the extent of in particular ≥80%, preferably ≥90%, more preferably ≥95%, yet more preferably ≥98%, in particular ≥99% and most preferably 100%.

The compositions of this invention can contain other components conventionally used in epoxy resin formulations such as impact modifiers and fillers as set out below.

Impact Modifiers

The composition may comprise an impact modifier. Impact modifiers are widely used to improve the impact strength of cured resin compositions with the aim to compensate their inherent brittleness and crack propagation. Impact modifier may comprise rubber particles such as CTBN rubbers (carboxyl-terminated butadiene-acrylonitrile) or core shell particles which contain a rubber or other elastomeric compound encased in a polymer shell. The advantage of core shell particles over rubber particles is that they have a controlled particle size of the rubber core for effective toughening and the grafted polymer shell ensures adhesion and compatibility with the epoxy resin composition. Examples of such core shell rubbers are disclosed in EP0985692 and in WO 2014062531.

Alternative impact modifiers may include methylacrylate based polymers, polyamides, acrylics, polyacrylates, acrylate copolymers, phenoxy based polymers, and polyethersulphones.

Fillers

In addition the composition may comprise one or more fillers to enhance the flow properties of the composition. Suitable fillers may comprise talc, microballoons, flock, glass beads, silica, fumed silica, carbon black, fibres, filaments and recycled derivatives, and titanium dioxide.

A prepreg resin formulation of the present invention can be prepared by uniformly mixing the curative of the invention, the resin and other additives using a pot mill, a ball mill, a bead mill, a roll mill, a homogenizer, Supermill, Homodisper, a universal mixer, Banbury mixer, a kneader, or the like.

Since the prepreg resin formulation of the present invention can be a one-component type that has both high storage stability and excellent thermosetting properties, it can be suitably used for applications which require long term storage or storage in unconditioned facilities at room temperature.

The resin formulations of this invention are particularly useful as the curable matrix for the production of fibre reinforced articles such as in prepregs that are used for the production of components for wind turbines and components for the aerospace industry such as aircraft wings and fuselages. The formulations may also be used in the production of automobile components and components used in shipping and in the production of sporting goods such as skis.

The invention is illustrated by the following Examples in which the following materials were used.

2,2-bis(3-amino-4-hydroxyphenyl)propane and 2,2-bis(3-amino-4-hydroxyphenyl), hexa-fluoro-propane were purchased from Tokyo chemicals Industry 3,3-diamino-4,4-dihydroxydipheynlsulfone (44-DDS) prepared as described in the literature 1,1-carbonyl-diimidazole was supplied by Apollo Scientific Dyhard UR500 (3,3'-(4-methyl-1,3-phenylene)bis(1,1-dimethylurea) purchased from Alzchem (see U.S. Pat. No. 9,663,609)

U52 (4,4' methylene diphenylene bis (N,N dimethylurea) from Emerald Performance Materials Company Orthohydroxyfenuron (OHFU) and N-(2-hydroxy-5-nitrophenyl)-N,N'-dimethylurea (5-NOHFU) were prepared as described in U.S. Pat. No. 4,404,356A MY721, a tetraglycidyldiaminodiphenylmethane epoxy resin, LY3581, a bisphenol F epoxy resin, MY0610 an epoxy resin based on triglycidyl-m-aminophenol and 4,4'-diphenyldiaminosulphone from Huntsman Advanced Materials Bisphenol A epoxy, Epikote 828 were obtained from Brenntag LY1556 an Araldite Epoxy resin from Huntsman 5003P a polyethersulfone thermoplastic supplied by Sumitomo polyamide particle supplied by Arkema All other reagents and solvents were supplied by Sigma-Aldrich The following test methods were used on the materials of the Examples.

Dynamic differential scanning calorimetry (DSC) was performed using a TA Q100 instrument to determine the uncured Tgs, of the resin and the onset and peak temperatures using a heating rate of 10° C./min, from −50 to 350° C. Dynamic DSC was also used to determine residual enthalpy in cured formulations for determination of % cure.

Isothermal differential scanning calorimetry (DSC) was performed using a DSC 1 from Mettler Toledo instruments to determine the time taken to reach the peak temperature reached during curing at various externally applied temperatures.

Dynamic mechanical analysis (DMA) was performed using a Q800 instrument on cured resin to determine glass transition temperatures at a heating rate of 5° C./min and at a frequency of 1 Hz, and at an amplitude of 30 μm.

Thermogravimetric analysis (TGA-DSC) was performed using a TGA/DSC 1 from Mettler Toledo to determine the melting point/decomposition temperature using a heating rate of 10° C./min, from 25 to 350° C. in air.

Dynamic and Isothermal rheology was performed using a MCR92 from Anton Paar. Dynamic rheology was performed with a heating rate of 2° C./min.

Outlifes were measured by monitoring the uncured Tg of the mixtures over time. The mixtures were stored in a temperature controlled incubator set at 23° C.

The following abbreviations are used.

PBOHFU-N,N'-[propylene(4-hydroxy3,1-phenylene)]bis(N,N-dimethyl)urea

FPBOHFU-N,N'-[hexafluoropropylene(4-hydroxy3,1-phenylene)]bis(N,N-dimethyl)urea

SBOHFU-N,N'-[sulfonyl(4-hydroxy-3,1-phenylene)]bis(N,N-dimethyl)urea

DOHFU-3,3'-(4,6-dihydroxy-1,3-phenylene)bis(1,1-dimethylurea)

OHFU-orthohydroxyfenuron

5-NOHFU-N-(2-hydroxy-5-nitrophenyl)-N,N'-dimethylurea

44-DDS 4,4-diaminodiphenyl sulfone

The results of the tests employed in the Examples are shown in FIGS. 1 to 4 hereof.

BRIEF DESCRIPTION OF THE SEVARAL VIEWS OF THE DRAWINGS

EXAMPLE 1

Figure 1:
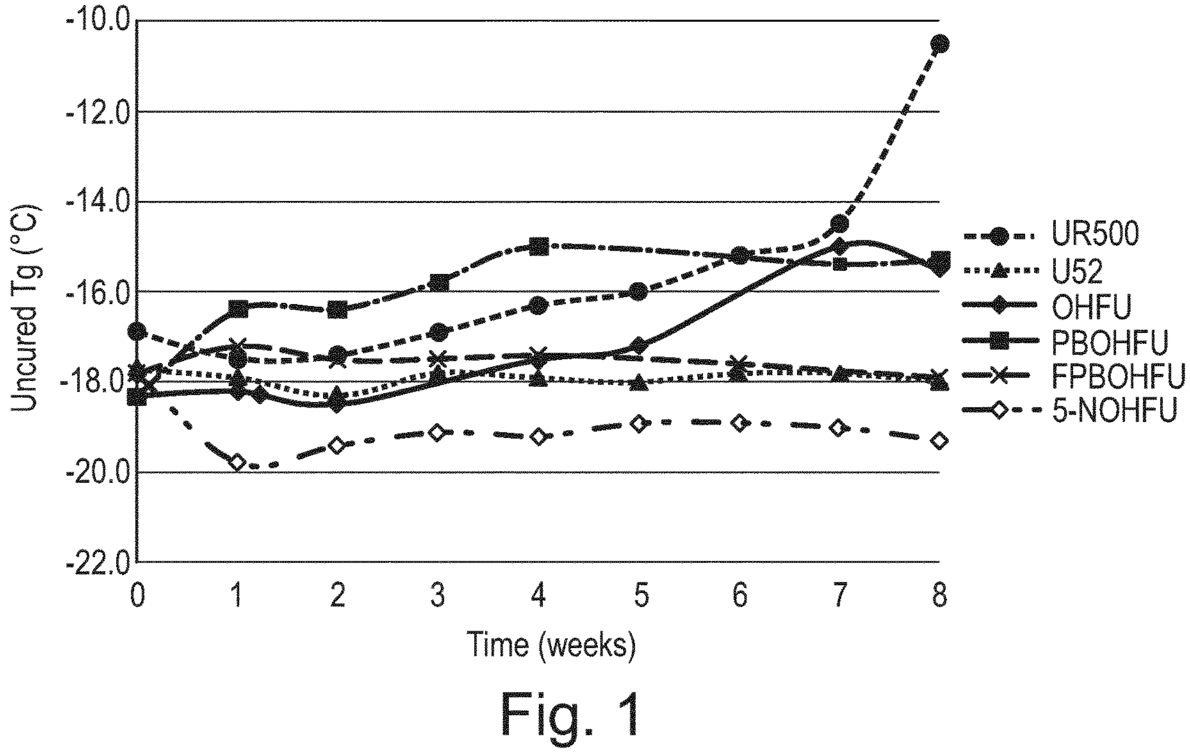
FIG. 1 is a graph which shows the outlife performace of the inventive resins relative to that of standard bisfunctional urones and monofunctional OHFUs using Tg data.

The production of N, N'-[propylene(4-hydroxy3,1-phenylene)]bis(N,N-dimethyl)urea, PBOHFU

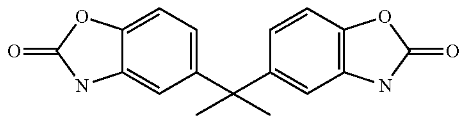 [SMILES: CC(C)(c1ccc2oc(=O)[nH]c2c1)c1ccc2oc(=O)[nH]c2c1]

The bisbenxoazolinone precursor of this formula was first prepared as follows to a 500 ml round bottom flask was added 25.2 g of 2,2-bis(3-amino-4-hydroxyphenyl)propane and 300 ml of dimethylacetamide. To the stirred solution was added 57.0 g of 1,1-carbonyldiimidazole portion-wise over 1 hour. The solution was heated to 60° C. and stirred at this temperature for 6 hours before cooling to room temperature. The solution was then poured in to 1 litre of deionised water to precipitate the product. To the mixture was added 4M hydrochloric acid until the solution had become slightly acidic. The precipitate was collected by vacuum filtration and washed with deionised water before drying in a vacuum oven at 60° C. overnight to give 29.7 g of a white powder, 98.0% yield, with a melting point of 278° C.

1H NMR (DMSO-d6): δ (ppm) 11.45 (bs, 2H, NH); 7.17 (d, 2H, Ar H); 6.96 (dd, 2H, Ar H); 6.82 (d, 2H, Ar H); 1.63 (s, 6H, CH3).

The PBOHFU of Formula

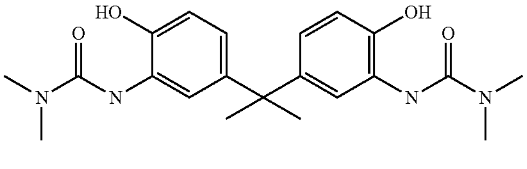

Was prepared from the precursor as follows to a 250 ml round bottom flask was added 29.7 g of 2,2-bis(3H-1,3-benzoxazol-2-one)propane precursor and 85 ml of 40 wt. % aqueous dimethylamine. The mixture was heated to 50° C. and stirred at this temperature for a total of 15 hours before cooling to room temperature. During this time, 80 ml of deionised water was added to dilute the solids content and aid stirring. The mixture was then transferred to a one neck round bottom flask and the excess dimethylamine removed on a rotary evaporator. The mixture was then acidified slightly using 4M hydrochloric acid. The precipitate was collected by filtration and washed with deionised water before drying in a vacuum oven at 60° C. overnight to give 36.1 g of a white powder, 94.3% yield, with a melting point of 189° C. (dec.).

The formula was confirmed by 1H NMR (DMSO-d6): δ (ppm) 9.62 (s, 2H, OH); 7.88 (s, 2H, NH); 7.29 (d, 2H, Ar H); 6.74 (dd, 2H, Ar H); 6.70 (d, 2H, Ar H); 2.93 (s, 12H, NCH3); 1.53 (s, 6H, CCH3);

EXAMPLE 2

Production of N,N-[hexafluoropropylene(4-hydroxy3,1-phenylene)]bis(N,N-dimethyl)urea, FPBOHFU

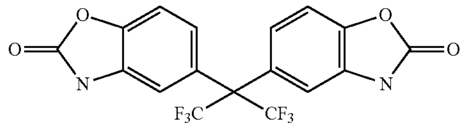 [SMILES: O=c1[nH]c2cc(C(c3ccc4oc(=O)[nH]c4c3)(C(F)(F)F)C(F)(F)F)ccc2o1]

The above benxoazolinone precursor was first prepared using 25.0 g of 2,2-bis(3-amino-4-hydroxyphenyl)hexafluoropropane, 175 ml of dimethylacetamide and 36.2 g of 1,1-carbonyldiimidazole in the same procedure set out in example 1 using a reaction time of 2.5 hours to give 26.2 g of a white powder, 91.8% yield, with a melting point of 322° C.

1H NMR (Methanol-d4): 0 (ppm) 7.26 (d, 2H, Ar H); 7.15 (d, 2H, Ar H); 7.09 (s, 2H, Ar H).

The urone was prepared using 26.2 g of 2,2-bis(3H-1,3-benzoxazol-2-one)hexafluoropropane, and 50 ml of 40 wt. % aqueous dimethylamine in the same procedure set out in example 1 using a reaction time of 2.5 hours to give 17.7 g of a white powder, 55.6% yield, with a melting point of 202° C. (dec.) to yield a product of the formula

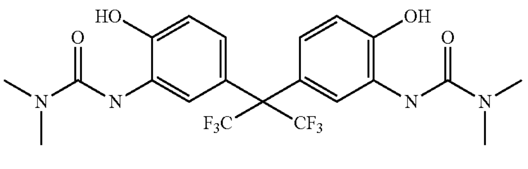

as confirmed by 1H NMR (DMSO-d6): δ (ppm) 10.29 (s, 2H, OH); 7.76 (s, 2H, NH); 7.72 (s, 2H, Ar H); 6.86 (d, 2H, Ar H); 6.81 (d, 2H, Ar H); 2.93 (s, 12H, NCH3);

EXAMPLE 3

Production of N,N'-[sulfonyl(4-hydroxy-3,1-phenylene)]bis(N,N-dimethyl)urea, SBOHFU

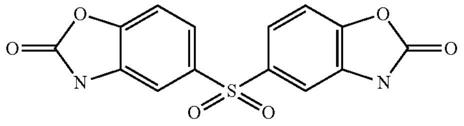 [SMILES: O=c1[nH]c2cc(S(=O)(=O)c3ccc4oc(=O)[nH]c4c3)ccc2o1]

The benxoazolinone precursor was first prepared using 5.6 g of 3,3-diamino-4,4-dihydroxydipheynlsulfone, 50 ml of dimethylacetamide and 10.3 g of 1,1-carbonyldiimidazole in the same procedure set out in example 1 using a reaction time of 4 hours to give 6.2 g of a white powder, 91.2% yield, with a melting point of >350° C. 1H NMR (DMSO-d6): δ (ppm) 12.13 (bs, 2H, NH); 7.74 (dd, 2H, Ar H); 7.57 (d, 2H, Ar H); 7.49 (d, 2H, Ar H);

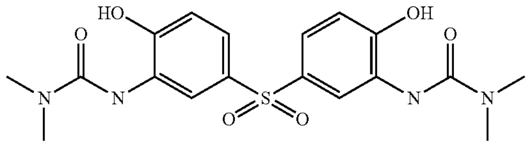

The urone was prepared using 6.2 g of 2,2-bis(3H-1,3-benzoxazol-2-one)sulfone, and 15 ml of 40 wt. % aqueous dimethylamine in the same procedure set out in example 1 using a reaction time of 7 hours to give 6.2 g of a tan coloured powder, 79.5% yield, with a melting point of 220° C. (dec.).

EXAMPLE 4

Production of 3,3'-(4,6-dihydroxy-1,3-phenylene)bis(1,1-dimethylurea), DOHFU

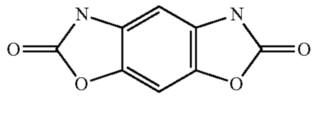 [SMILES: O=c1[nH]c2cc3[nH]c(=O)oc3cc2o1]

The bisbenxoazolinone precursor was first prepared. To a 500 ml round bottom flask was added 25.0 g of 4,6-diaminoresorcinol dihydrochloride and the flask placed under an inert atmosphere of nitrogen. 300 ml of dimethylacetamide was then added. To the stirred suspension was added 16.0 ml of triethylamine drop-wise followed by 63.4 g of 1,1-carbonyldiimidazole portion-wise over 1 hour. The suspension was heated to 60° C. and stirred at this temperature for 2 hours before cooling to room temperature. The mixture was then poured in to 1 L of deionised water to precipitate to the product. To the mixture was added 4M hydrochloric acid until the solution had become slightly acidic. The precipitate was collected by vacuum filtration and washed with deionised water before drying in a vacuum oven at 60° C. overnight to give 21.8 g of an off-white powder, 96.9% yield, with a melting >350° C. 1H NMR (DMSO-d6): 0 (ppm) 11.25 (bs, 2H, NH); 7.44 (s, 2H, Ar H); 6.76 (s, 2H, Ar H);

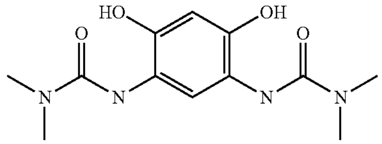

The urone was prepared using 10.1 g of [1,3]-oxazolo[4,5-F][1,3]benzoxazole-2,6-(3H,5H)-dione, and 40 ml of 40 wt. % aqueous dimethylamine in the same procedure set out in example 1 using a reaction time of 2.5 hours. The product was purified by dissolving in 100 ml of hot dimethylacetamide and filtering. The filtrate was then poured in to 250 ml of deionized water. The precipitate was collected by filtration and washed with deionized water before drying in a vacuum oven at 60° C. overnight to give 11.4 g of a burgundy powder, 77.0% yield, with a melting point of 233° C. (dec.).

1H NMR (DMSO-d6): δ (ppm) 9.47 (s, 2H, OH); 7.70 (s, 2H, NH); 7.28 (s, 1H, Ar H); 6.32 (d, 1H, Ar H); 2.94 (s, 12H, NCH3);

EXAMPLE 5

The products of Examples 1 and 2 were used as curatives for an Epoxy resin and compared with standard bisfunctional urones UR500 and U52, and with OHFU and NOHFU as monofunctional orthohydroxyfenurons. The urones were dispersed in the epoxy resin Epikote 828 so that there is an equivalent ratio of urone functionalities to epoxy resin groups=5.6 mol % of urone groups to epoxy groups.

TABLE 1

| Epoxy weight (g) | Urone | Urone weight (g) |
|---|---|---|
| 11.40 | UR500 | 0.44 |
| 11.40 | U52 | 0.57 |
| 11.40 | OHFU | 0.60 |
| 11.40 | 5-NOHFU | 0.75 |
| 11.40 | PBOHFU | 0.68 |
| 11.40 | FPBOHFU | 0.87 |

The mixtures were cured in a fan oven at 150° C. for 1 hour with 1° C./min temperature increase to reach 150° C. The samples were also postcured at 180° C. for 2 hours to achieve full cure. The results in Table 2 show that the use of the urones of this invention show improved ultimate Tg compared the standard urones and the monofunctional OHFUs.

TABLE 2

| Urone | Tg 150° C. cure | Tg 180° C. postcure (° C.) |
|---|---|---|
| UR500 | 94 | 96 |
| U52 | 94 | 96 |
| OHFU | 97 | 98 |
| 5-NOHFU | 79 | 98 |
| PBOHFU | 109 | 110 |
| FPBOHFU | 83 | 100 |

The reactivity was measured at various cure temperatures by the time to peak from isothermal DSC and as Table 3 shows the PBOHFU of the invention performs in a similar manner if not slightly better than the non-hydroxy phenyl bisfunctional urea U52.

TABLE 3

| | Time to peak at T = (mins) | | | |
|---|---|---|---|---|
| Urone | 80° C. | 90° C. | 110° C. | 130° C. |
| U52 | 244 | 118 | 36 | 14 |
| PBOHFU | 230 | 99 | 28 | 11 |

The outlifes of the mixtures were tracked by monitoring the uncured Tg of the mixtures when held at 23° C. over time. The graph which is FIG. 1 hereof shows that the outlife performance is similar to both that of the standard bisfunctional urones and the monofunctional OHFUs.

Furthermore, as Table 4 shows increasing the content of the bis OHFUs of this invention in the epoxy resin from 5.6 to 10 mol % of urone groups to epoxy groups improves the Tg to a greater extent than when using the monofunctional OHFUs.

TABLE 4

| Epoxy weight (g) | Urone | Urone weight (g) | Tg 150° C. cure | Tg 180° C. postcure (° C.) |
|---|---|---|---|---|
| 11.40 | OHFU | 1.06 | 101 | 104 |
| 11.40 | 5-NOHFU | 1.37 | 101 | 106 |
| 11.40 | PBOHFU | 1.22 | 116 | 121 |
| 11.40 | FPBOHFU | 1.55 | 101 | 108 |

As shown the PBOHFU exhibited an improved Tg compared the monofunctional OHFU. OHFU shows an increase of only 6° C. in ultimate Tg when added a 10 mol % compared to 5.6 mol % whereas PBOHFU shows and 11° C. increase at 10 mol % compared to 5.6 mol %.

EXAMPLE 6

The product of Example 1 was used as a curative for an Epoxy resin and compared with standard bisfunctional urones UR500 and U52 and with OHFU as a monofunctional orthohydroxyfenuron. The urones were dispersed in the epoxy resin MY721 so that there is an equivalent ratio of urone functionalities to epoxy resin groups=5.6 mol % of urone groups to epoxy groups.

TABLE 5

| MY721 (g) | Urone | Urone weight (g) |
|---|---|---|
| 11.40 | UR500 | 0.74 |
| 11.40 | U52 | 0.95 |
| 11.40 | OHFU | 1.01 |
| 11.40 | PBOHFU | 1.12 |

The mixtures were cured in a fan oven at 180° C. for 2 hours with 1° C./min temperature increase to reach 180° C. The results in Table 6 show that the use of the urones of this invention show improved ultimate Tg postcure compared the standard urones and the monofunctional OHFU.

TABLE 6

| Urone | Tg 180° C. cure |
|---|---|
| UR500 | 175 |
| U52 | 168 |
| OHFU | 185 |
| PBOHFU | 190 |

Figure 2:
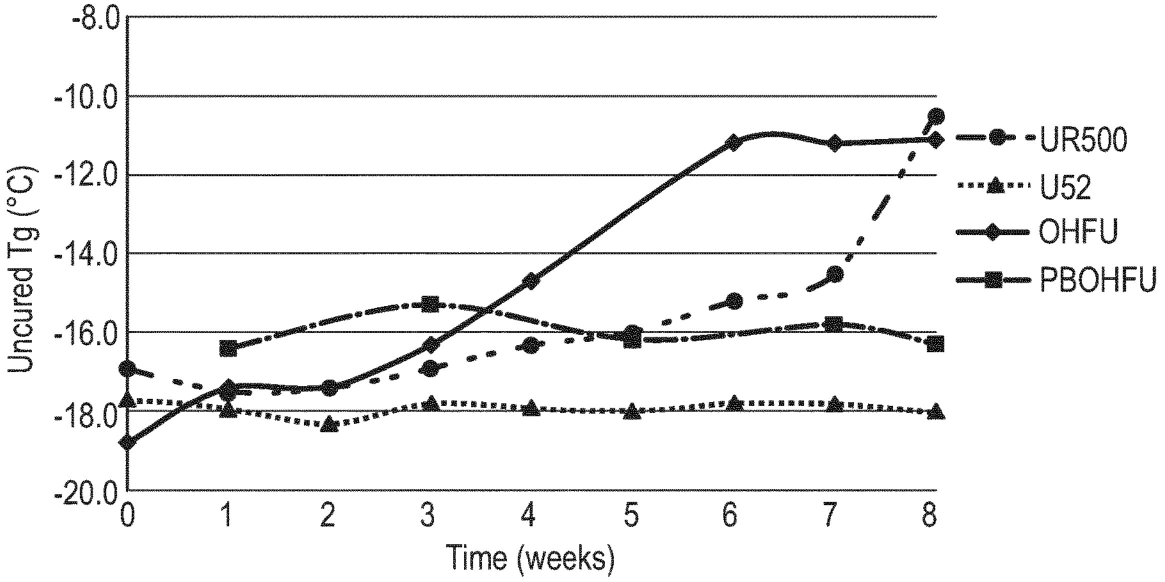
FIG. 2 is a graph which shows the outlife performace of the inventive resins relative to that of standard bisfunctional urones and monofunctional OHFUs using Tg data.

The outlifes of the mixtures of Table 5 were tracked by monitoring the uncured Tg of the mixtures when held at 23° C. over time. The graph which is FIG. 2 hereof shows that the outlife performance is similar for the products of the invention to both that of the standard bisfunctional urones and slightly better than the monofunctional OHFUs.

Figure 3:
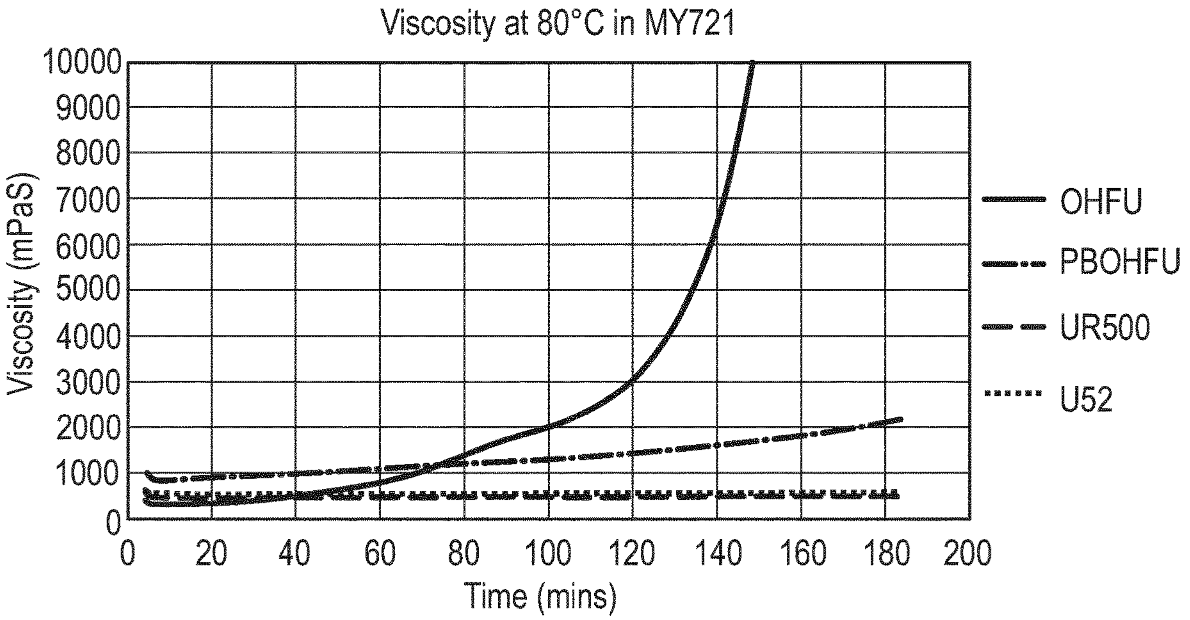
FIG. 3 is a graph which shows outlife performance of the inventive resins relative to that of standard bisfunctional urones and monofunctional OHFUs using viscosity data.

The latency of the mixtures at 80° C. was monitored by isothermal rheology over a 3-hour time frame. The graph which is FIG. 3 hereof shows that the PBOHFU of the invention shows better latency performance at 80° C. than the monofunctional OHFU and approaches that of the standard bisfunctional urones UR500 and U52.

EXAMPLE 7

The products of Examples 1 and 2 were used as accelerators for a 4,4-DDS curing system as shown in Table 7 compared with standard bisfunctional urones UR200 and U52 and with OHFU as a monofunctional orthohydroxyfenuron.

TABLE 7

| Component | Composition (wt. %) |
|---|---|
| MY0610 | 27.64 |
| LY1556 | 24.45 |
| 5003P | 15.00 |
| Polyamide particle | 13.50 |
| 4,4-DDS | 18.40 |
| Urone | 1.00 |

The mixtures were cured in a fan oven at 180° C. for 45, 75 and 120 minutes, 1° C./min temperature increase to reach 180° C. The results in Tables 8 and 9 show, whilst the PBOHFU and FPBOHFU of the invention show similar effects of cure acceleration in terms of % cure, they exhibit improved Tgs across all cure cycle times compared to the standard urones and the monofunctional OHFU.

TABLE 8

| | Tg (° C.) after 180° C. cure for | | |
|---|---|---|---|
| Accelerator | 45 minutes | 75 minutes | 120 minutes |
| UR500 | 130 | n/a | 136 |
| U52 | 131 | n/a | 143 |
| OHFU | 138 | n/a | 145 |
| PBOHFU | 151 | 149 | 151 |
| FPBOHFU | 156 | 162 | 167 |

TABLE 9

| | % cure after 180° C. cure for | | |
|---|---|---|---|
| Accelerator | 45 minutes | 75 minutes | 120 minutes |
| UR500 | 96.1 | n/a | 97.5 |
| U52 | 94.6 | n/a | 98.5 |
| OHFU | 96.1 | n/a | 98.4 |
| PBOHFU | 97.4 | 97.8 | 97.8 |
| FPBOHFU | 96.4 | 97.5 | 99.0 |
| No accelerator | 81.1 | 85.1 | 91.8 |

The composition of the formulation was modified by reducing the urone content to that shown in Table 10 and Tables 11 and 12 show how decreasing the content of the bis OHFUs of this invention in the DDS curing system lead to a further improvement in Tg whilst still offering good acceleration across all cure cycle times.

TABLE 10

| Component | Composition (wt. %) |
|---|---|
| MY0610 | 27.84 |
| LY1556 | 24.63 |
| 5003P | 15.00 |
| Polyamide particle | 13.50 |
| 4,4-DDS | 18.53 |
| Urone | 0.50 |

TABLE 11

| | Tg (° C.) after 180° C. cure for | | |
|---|---|---|---|
| Accelerator | 45 minutes | 75 minutes | 120 minutes |
| PBOHFU | 160 | 166 | 176 |
| FPBOHFU | 163 | 173 | 180 |

TABLE 12

| | % cure after 180° C. cure for | | |
|---|---|---|---|
| Accelerator | 45 minutes | 75 minutes | 120 minutes |
| PBOHFU | 96.8 | 97.8 | 99.0 |
| FPBOHFU | 94.1 | 96.0 | 97.6 |
| No accelerator | 81.1 | 85.1 | 91.8 |

Figure 4:
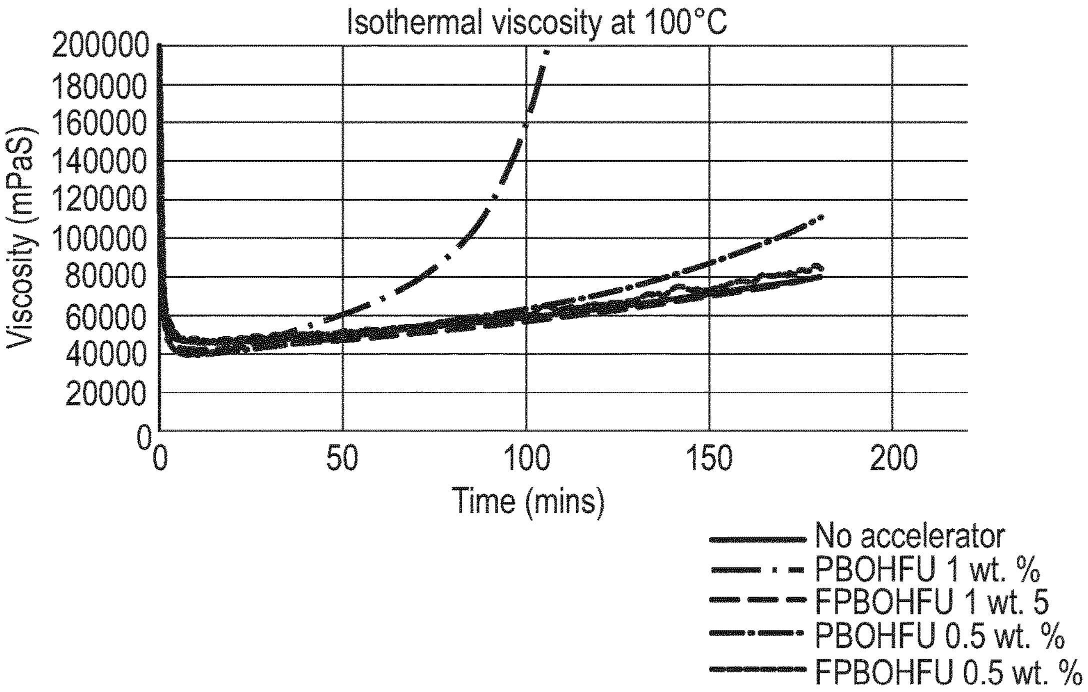
FIG. 4 is a graph which shows outlife performance of the inventive resins relative to that of standard bisfunctional urones and monofunctional OHFUs using viscosity data.

The latency of the mixtures at 100° C. was monitored by isothermal rheology over a 3-hour time frame. The graph which is FIG. 4 hereof shows that the FBOHFU and PBOHFU of the invention show that the latency performance at 100° C. is unchanged for FBOHFU, at both the 1% and 0.50% loadings, compared to the unaccelerated formulation.

The invention claimed is:

1. A process for the production of an article comprising curing a prepreg by an externally applied temperature of 60° C. to 190° C.; wherein said prepreg comprises:

(a) bisorthohydroxy aromatic urone of formulae:

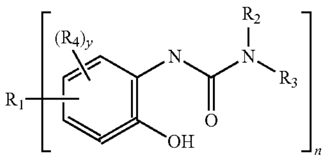

wherein $R_1$ is selected from S, SO2, SO, P, PX, N, NH, or NX, P═O(—OH), P═O(—OX), C═O, a substituted or unsubstituted linear or branched aliphatic radical, or an unsubstituted, halo substituted and/or alkyl substituted aromatic radical and n is a number from 2 to 20;

wherein X is a substituted or unsubstituted linear or branched aliphatic radical, or an unsubstituted, halo substituted and/or alkyl substituted aromatic radical;

wherein $R_2$ and $R_3$ is at each occurrence, independently of one another, selected from an alkyl, cycloalkyl, alkenyl, cycloalkenyl, or aralkyl group, which may be substituted by a halogen atom or by a hydroxyl or cyano group; and and wherein $R_4$ is at each occurrence, independently of one or another, selected from H, $NH_2$, $NO_2$, nitrile, a halogen, linear or ranched aliphatic radical, or an unsubstituted, halo substituted and/or alkyl substituted aromatic radical, and Y=1 to 3; and wherein wherein the bisorthohydroxy aromatic urone comprises 0.1 to 20 wt % of said prepreg; further comprising a fibrous reinforcement material selected from a woven fabric, a multi-axial fabric, individual fibre tows, and mixtures thereof.

2. The process according to claim 1 wherein the curing is performed in a press.

* * * * *